United States Patent [19]
Kelln

[11] Patent Number: 4,680,164
[45] Date of Patent: Jul. 14, 1987

[54] CENTRIFUGAL ANALYZER
[75] Inventor: Norman G. Kelln, Spokane, Wash.
[73] Assignee: Fisher Scientific Company, Pittsburgh, Pa.
[21] Appl. No.: 756,860
[22] Filed: Jul. 18, 1985
[51] Int. Cl.[4] ............................................. G01N 21/07
[52] U.S. Cl. ...................................... 422/72; 422/63; 422/65; 422/104; 494/40; 494/41
[58] Field of Search ...................... 422/64, 65, 72, 73, 422/63, 104, 38, 40; 494/41; 222/42, 48, 47; 141/1, 68

[56] References Cited
U.S. PATENT DOCUMENTS

| 3,586,484 | 6/1971 | Anderson. | |
|---|---|---|---|
| 3,617,222 | 11/1971 | Matte | 422/73 |
| 3,798,459 | 3/1974 | Anderson. | |
| 3,813,031 | 5/1974 | Anderson. | |
| 3,916,152 | 10/1975 | Hinman. | |
| 4,030,834 | 6/1977 | Bauer et al. | 422/72 |
| 4,314,970 | 2/1982 | Stein. | |
| 4,344,768 | 8/1982 | Parker et al. | 422/72 |
| 4,360,360 | 11/1972 | Chiknas. | |
| 4,456,581 | 6/1984 | Edelmann. | |
| 4,495,149 | 1/1985 | Iwata et al. | 422/65 |
| 4,580,897 | 4/1986 | Nelson et al. | 422/64 |

Primary Examiner—Michael S. Marcus

[57] ABSTRACT

An analysis system of the centrifugal analyzer type has an analysis station for receiving a multi-cuvette rotor unit with means at the analysis station for performing analyses on the contents of a plurality of cuvettes of a multi-cuvette rotor unit concurrently, and means at the analysis station for spinning the rotor unit. Rotor hold down means at the analysis station includes disc structure for seating engagement with loading ports of the rotor unit at the analysis station, a disc support for allowing the disc to rotate freely in alignment with the drive axis of the drive mechanism, and mechanical means for moving the freely rotatable disc between an operative position in seating engagement with the loading ports of the rotor unit and a second position spaced from the seated position.

14 Claims, 6 Drawing Figures

CENTRIFUGAL ANALYZER

This invention relates to analysis systems, and to systems for the concurrent analyses of a plurality of fluid samples, and has particular application to apparatus for the analysis of constituents of biological fluids such as blood.

Known chemical analyzer systems perform analyses concurrently with the use of plural compartment types of multi-cuvette analysis units. Among such analyzers is the centrifigal type of clinical analyzer which uses a multi-cuvette rotor unit. Such centrifugal analyzers perform a variety of analytical tests including, for example, glucose, creatinine, CPK, SGOT, and enzyme immuno assays measurements, those tests involving kinetic and endpoint reactions and being performed rapidly, accurately, and inexpensively. The multi-cuvette rotor unit or transfer disc used with the centrifugal analyzer has a plurality of spaced, elongated radially extending cuvettes arranged in circumferential array. In a typical rotor, each cuvette has a first chamber for initially holding a first reactant (frequently a sample of blood or other biological fluid) and a second chamber for initially holding one or more different reactants, each chamber having an associated loading port. After cuvettes of the rotor are loaded with samples to be analyzed and reagents, the rotor is transferred to an analysis system where the rotor is spun to transfer the reactants by centrifugal force to analysis regions at the outer portions of the several rotor cuvettes for mixing, reaction and subsequent analysis by photometric or other analysis technique. In an exemplary rotor spinning sequence, at the start of analysis the rotor is first spun at one hundred rpm, then accelerated to about four thousand rpm in about one second, then braked to a full stop, and then brought up to a speed of approximately six hundred rpm for an analysis interval of several minutes duration.

The rotor unit must be secured on the analyzer drive table and the loading ports closed to avoid analysis problems due to artifacts such as sample mixture evaporation and temperature transitions while the rotor is being spun during analysis, and to discharge of reagents through the loading ports. In conventional analyzer systems of this type, a manual type of screw-down device is used to secure the rotor on the drive table at the analysis station.

In accordance with the invention, there is provided an analysis system of the centrifugal analyzer type which has an analysis station for receiving a multi-cuvette rotor unit with means at the analysis station for performing analyses on the contents of a plurality of cuvettes of a multi-cuvette rotor unit concurrently, and means at the analysis station for spinning the rotor unit. Rotor hold down means at the analysis station includes disc structure for seating engagement with loading ports over rotor unit at the analysis station, a disc support for allowing the disc to rotate freely in alignment with the drive axis of the drive mechanism, and mechanical means for moving the freely rotatable disc between an operative position in seating engagement with the loading ports of the rotor unit and a second position spaced from the seated position.

In a particular embodiment, a table at the analysis station is adapted to receive a centrifugal analyzer rotor that has a smooth hard upper body surface in which two circumferential arrays of cuvette loading ports are defined, and sensor means provides output signals indicative of the angular position of the rotor at the analysis station as it is being spun by the table drive mechanism. The hold down mechanism includes a support shaft aligned with the rotation axis of the drive mechanism, and accommodation means for seating the disc member on the rotor to close the loading ports includes a self-aligning spherical bearing. The hold down assembly includes a port closing member of material that has a durometer of about 40 (Shore A) and a surface roughness of greater than twenty microinches, while the hardness of the rotor surface in which the loading ports are disposed is greater than 50 Rockwell$_M$. A spring member imposes a biasing force of about fifty grams on the port closing disc member, that biasing force firmly seating the disc on the rotor surface to close the loading ports; and cam means moves the disc between the seated and second positions along the rotation axis of the table drive mechanism so that the rotor ports are closed in the operative (hold-down) position and the hold-down assembly is readily released from the rotor after analysis.

The analyzer system in that embodiment includes a supply station for furnishing a series of multi-cuvette rotor units, and transport mechanism movable between the supply, loading and analysis stations for transporting rotor units in correlated orientation between those stations. Each rotor defines a circumferential array of elongated radially extending cuvettes, each elongated cuvette including structure defining a first chamber for receiving a first constituent and a loading port through which the first constituent is introduced into the first chamber, structure defining a second chamber region for receiving a second constituent, a second loading port through which the second constituent is introduced into the second chamber region, divider structure between the first and the second chamber regions that defines a transfer passage between the first and second chamber regions through which the first constituent may be flowed into the second chamber region for forming a reaction product with the second constituent, and structure defining an analysis region adjacent the radially outer wall of the cuvette where the reaction product is subjected to analysis. The drive means at the analysis station spins a rotor at least one thousand rpm for combining sample and reagent materials in separate compartments of the several cuvettes. The hold down disc has low inertial mass, seats firmly on the rotor to close the loading ports and obstruct air flow through the cuvette compartments during analysis, and releases readily from the rotor after analysis is completed.

Other features and advantages of the invention will be seen as the following description of a particular embodiment progresses, in conjunction with the drawings, in which.

DESCRIPTION OF PARTICULAR EMBODIMENT

Figure 1:
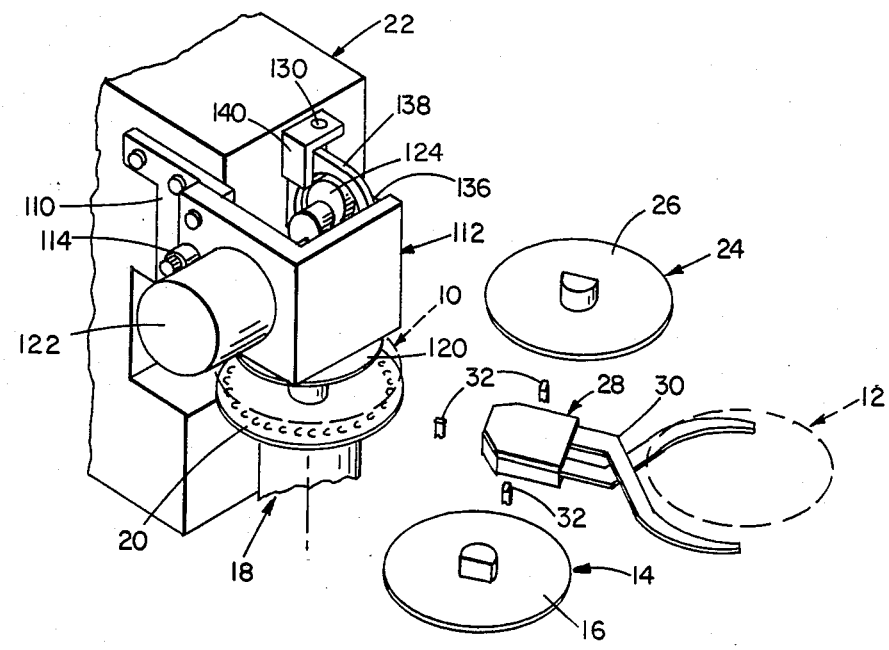
FIG. 1 is a perspective view of portions of a centrifugal analyzer system in accordance with the invention.
Figure 2:
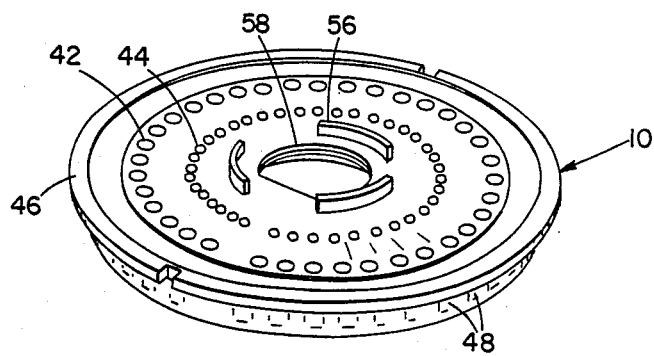
FIG. 2 is a perspective view of an analyzer rotor used in the system of FIG. 1.

The analysis system shown in FIG. 1 is of the centrifugal analyzer type and utilizes a rotor assembly 10 of the type shown in FIG. 2 that is transported within a thermally isolated storage compartment between supply station 12; loading station 14 that has rotor support table 16 that is indexed by a stepping motor (not shown); analysis station 18 that includes rotor support table 20 and cooperating optics module 22; and auxiliary station 24 that includes rotor support table 26. Rotor transport mechanism 28 includes articulated rotor transport arm assembly 30 that is rotated between supply station 12, loading station 14, analysis station 18, and auxiliary station 24 and three actuator members 32 in the form of double flatted cam members which cooperate with arm assembly 30 to grasp and release rotors 10 as they are transported between stations 12, 14, 18 and 24. Further details of that analyzer system may be had with reference to copending application Ser. No. 706,073 filed Feb. 27, 1985 entitled CUVETTE HANDLING, the disclosure of which is incorporated herein by reference.

With reference to FIG. 2, the rotor assembly 10 employed in this analyzer has a diameter of about ten centimeters, an overall body height of about one centimeter, and is formed of ultraviolet transmitting polymeric (acrylic) material that has appropriate transparency, chemical resistance and optical characteristics for photometric analysis, the hardness of the smooth upper surface of the rotor 10 being about 75 Rockwell$_M$. Rotor assembly 10 defines a circumferential array of thirty-nine individual analysis cuvettes 40, each of which has corresponding inner and outer loading ports 42, 44. Rotor 10 has circumferential flange structure 46, a peripheral surface in which a series of optical windows 48 are defined, upper and lower optical window channels 50, 52 (FIG. 6) between which an analysis region 54 of each cuvette 40 is defined; a series of three arcuate spacer webs 56 and a central D-shaped aligning aperture 58. Further details of rotor 10 may be had with reference to copending application Ser. No. 615,501 filed May 31, 1984 entitled CUVETTE ROTORS FOR CENTRIFUGAL ANALYZERS, the disclosure of which is incorporated herein by reference.

Figure 3:
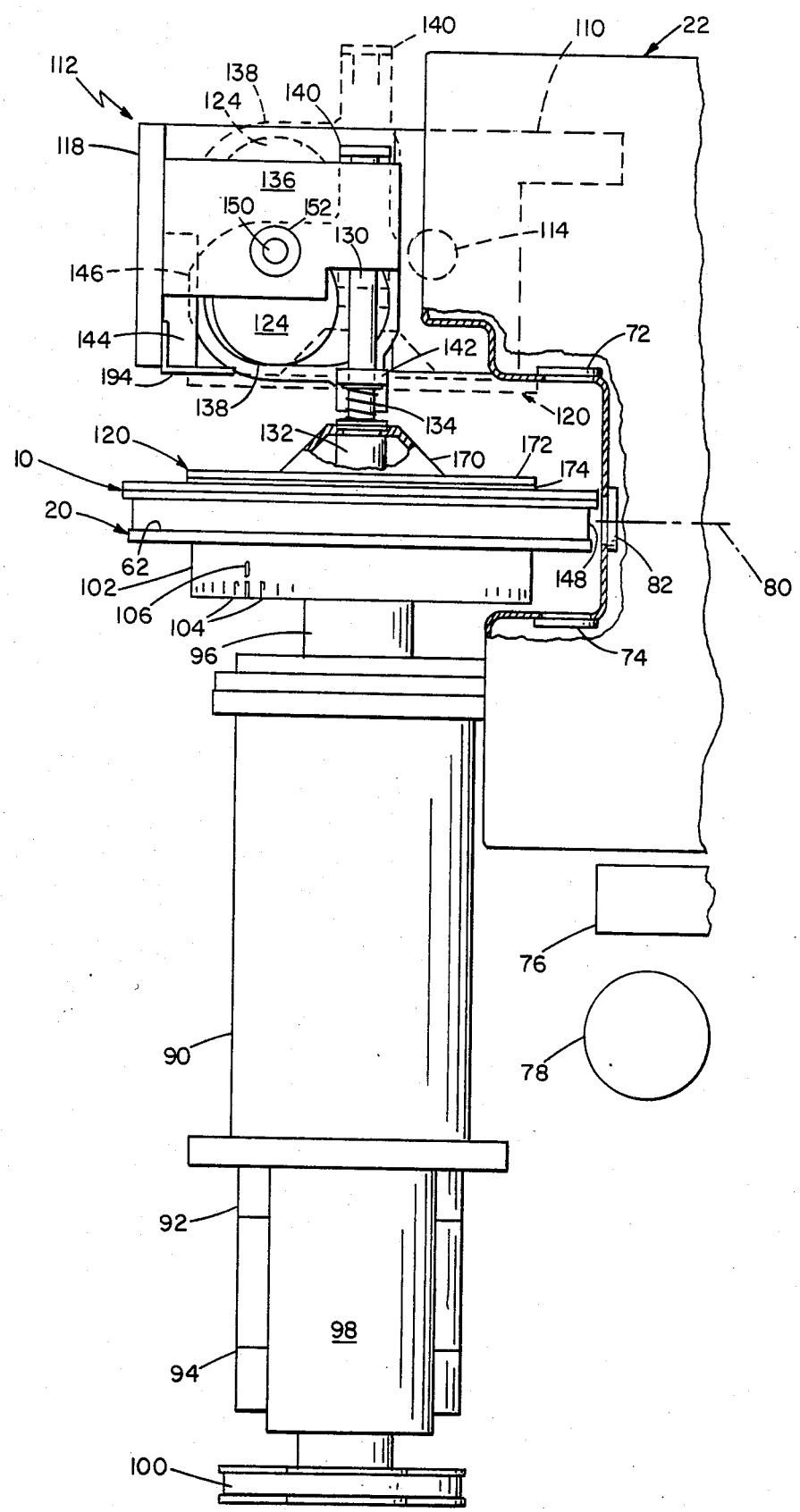
FIG. 3 is a side elevational view (with parts broken away) of the analysis station shown in FIG. 1.
Figure 4:
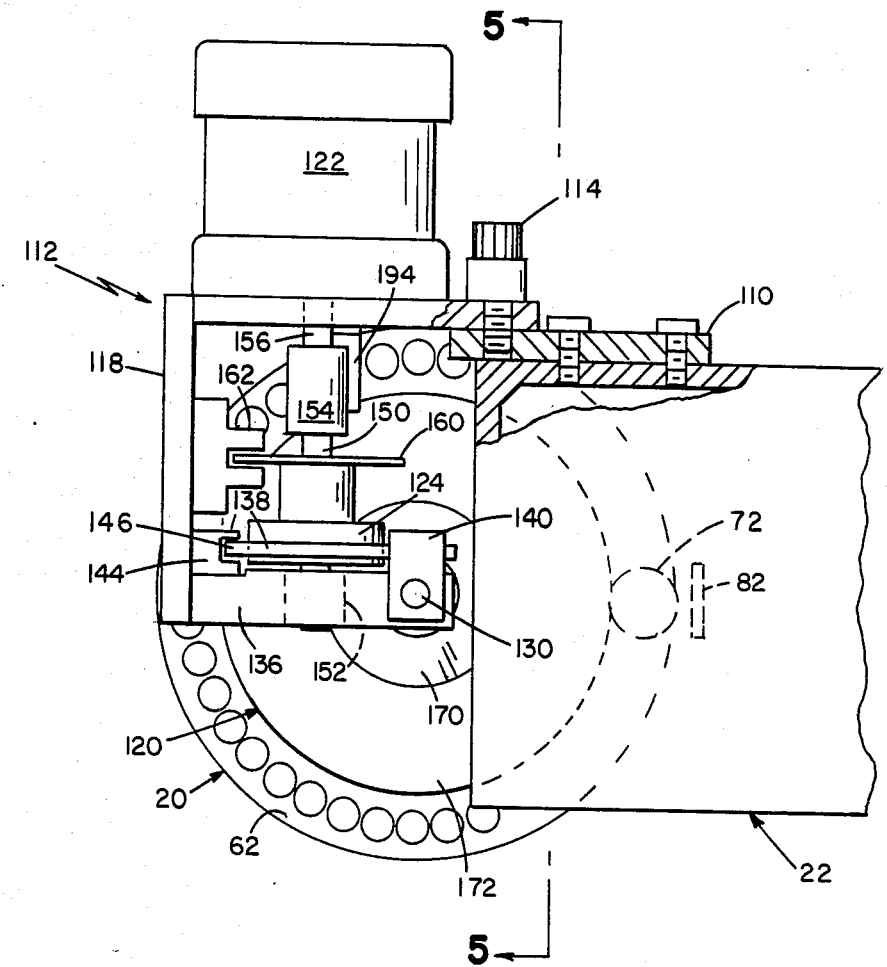
FIG. 4 is a top plan view of the analysis station of the analyzer system shown in FIG. 1.

With reference to FIGS. 3 and 4, apparatus at analysis station 18 includes rotor support table 20 that has D-shaped orienting hub 60 and a circumferential support surface 62 that has a series of thirty-nine apertures 64 around its periphery and an aligning projection 66 which cooperates in a socket recess in the base of the body of rotor 10. The thirty-nine holes 64 around the edge of analysis table 20 (in an absorption mode of analysis) allow radiation to pass along a vertical path 70 from upper optics module window 72 through the analysis regions of the cuvettes 40 of the rotor 10 on table 20, lower optics module window 74, and filter wheel 76 for sensing by photomultiplier tube 78. In a second mode (fluorescence or light-scattering), a beam of light 80 from a xenon lamp passes through optics module window 82 and the end windows 48 of the rotor 10 for producing secondary emissions that pass through the entrance window 74 directly below the rotor table 20 and through the filter 76 to the photomultiplier tube 78.

DC motor 90 is adapted to drive rotor table 20 at high speed for sample-reagent mixing prior to analysis and at a constant speed (600 rpm) during analysis; braking action is provided by 24 volt DC brake 92 that generates fifteen inch pounds of braking torque and stops rotation of table 20 in less than one-quarter revolution; and clutch 94 connects the analysis station table drive shaft 96 to stepping motor 98 via belt drive 100.

Table 20 has an annular depending skirt 102 that has a series of 80 timing slots 104 and an index slot 106. Sensors monitor slots 104, 106 and provide position signals to the analyzer control during analysis of the contents of the rotor cuvettes 40.

Mounted on optics module 22 is support plate 110 to which a rotor hold down assembly 112 is secured by fastener 114. The rotor hold down assembly includes a support frame 118 that carries hold down disc assembly 120 and stepping motor 122 that rotates cam 124 to raise and lower disc assembly 120.

Figure 5:
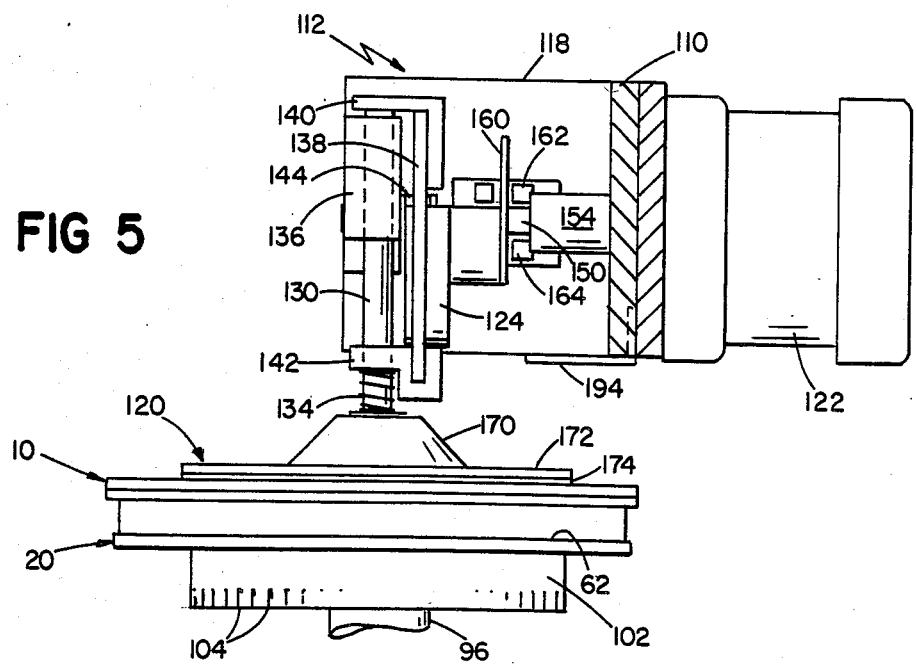
FIG. 5 is a side elevational view (with parts broken away) similar to FIG. 3 showing components thereof in a second position.

Further details of the hold down mechanism may be seen with reference to FIGS. 3-5. Hold down disc assembly 120 is secured to vertical support shaft 130 by means of self-aligning bearing assembly 132 and disc spring 134. Shaft 130 extends through a vertical guide bore in support plate 136 and is fixed to cam follower member 138 by upper and lower brackets 140, 142. Vertical guide member 144 receives the edge 146 of cam follower 138 opposite brackets 140, 142. Cylindrical cam 124 (about 2.5 centimeters in diameter) is part of shaft 150, one end of shaft 150 being supported in bearing 152 carried by support plate 136 and its other end being connected by coupling 154 to drive shaft 156 of stepping motor 124. Mounted on shaft 150 is sensor disc 160 that cooperates with optical sensors 162, 164 to signal the upper position of hold down disc assembly 120 (FIG. 3) and its lower (seating) position (FIG. 5).

Rotor hold down assembly 120 includes an aluminum member that has conical hub portion 170 and surrounding flange portion 172 to which is secured disc 174 of 43 durometer (Shore A) silicone rubber. Flange portion 172 has an outer diameter of about 8.8 centimeters and a thickness of about 2.3 millimeter while disc 174 has an inner diameter of about four centimeters, an outer diameter of about 8.8 centimeters and a thickness of about 1.5 millimeters. Annular port closing portions 176, 178 are each about 0.7 centimeter wide and have a waffled surface (providing a surface finish of about sixty microinches). Self-aligning bearing assembly 132 has flange 184 which is secured to hub 170 and a body 182 which carries nylon ring 186 that engages oil-impregnated sintered-bronze cylindrical spherical bearing 190. The lower end of shaft 130 extends through bearing 190 and is secured by ring 192. Coil spring 134 between flange 184 and bracket 142 exerts a downward biasing force of about fifty grams on the hold down assembly. Aligning members 194 are secured to optics module 22 which engage flange portion 172 in the upper position of hold-down disc assembly 120 to position disc portions 176, 178 generally parallel to the rotor receiving surface 62 of table 20.

Figure 6:
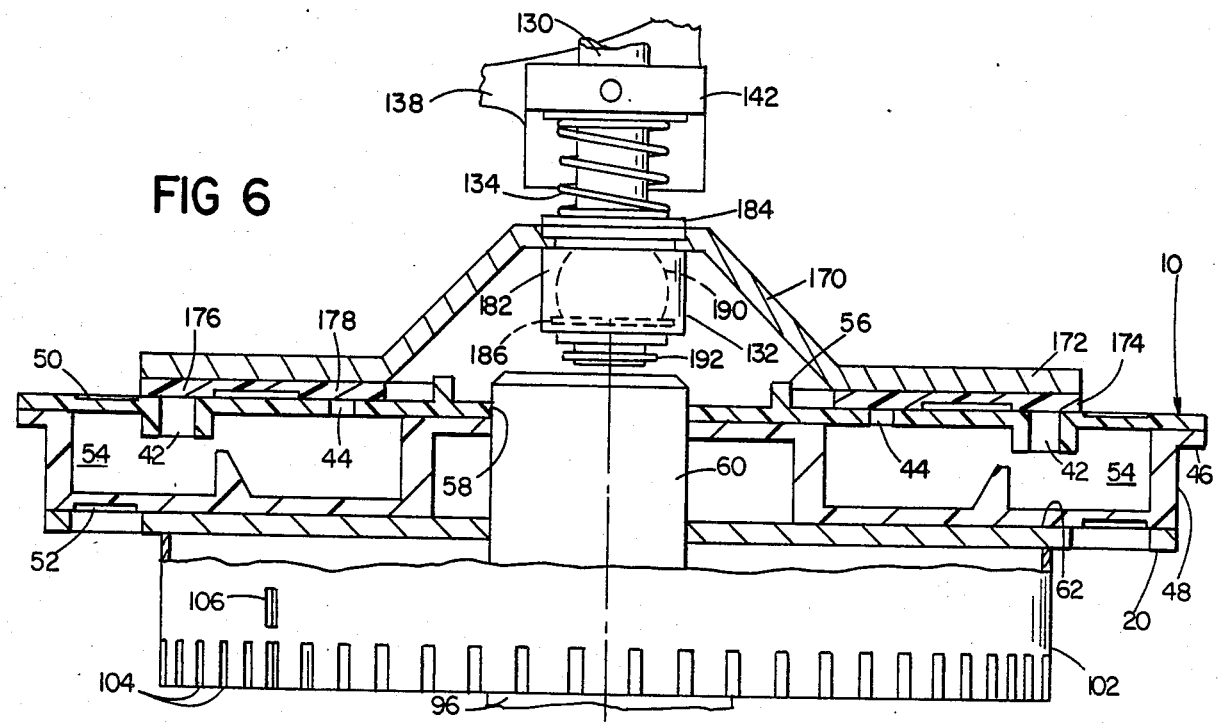
FIG. 6 is a sectional view taken along the line 6—6 of FIG. 4 showing further details of apparatus at the analysis station.

With reference to FIGS. 3 and 5, in an analysis sequence, table 20 is indexed to appropriate orientation by motor 98 and the loaded rotor 10 whose cuvettes contain sample and reagent materials to be analyzed is moved from loading station 14 and placed on table 20 by transport mechanism 28 (as described in above referenced application Ser. No. 706,073). Stepping motor 122 then rotates cam 124 180° to the position shown in FIG. 5 to seat disc 174 on the upper surface of the rotor on table 20 as indicated in FIG. 6 with the disc portions 176, 178 closing the loading ports 42, 44 respectively. In this position, spring 134 biases disc 174 against the upper surface of the mounted rotor 10 with a force of about fifty grams. The axes of shafts 96 and 130 are in alignment, and the bearing assembly 132 insures aligned seating so that table 20 with its supported rotor 10 and the hold down disc assembly 120 are free to rotate as a unit, that rotating unit having a total inertia of about 0.05 pound-inches$^2$.

With the rotor held on table 20 by the hold down assembly 120, as indicated in FIGS. 5 and 6, and with stepper motor 98 decoupled from drive shaft 96 by clutch 94, the analysis table drive motor 90 is accelerated to approximately 3,600 rpm to transfer the reactant materials from the inner region of each cuvette into the outer region and the analysis region 54 for combining; the assembly is then rapidly braked by brake 92 to enhance mixing of the contents of the several analysis cuvettes 40; and then the table-rotor-hold down disc assembly is driven at approximately 600 rpm by DC motor 90 with concurrent generation of position signals from the timing slots 104 and sensing of the radiation beam passing through window 74 by photomultiplier tube 78 to monitor the several chemical reactions.

After analysis of the rotor 10 is completed (a typical analysis cycle having a duration of about five minutes), motor 124 rotates cam 122 to release the hold down disc 120 and as that disc is being raised, brake 94 rapidly stops rotation of the table 20 and rotor 10, the relative torque of hold down assembly 120 and its inertia overcoming any residual adherance between rotor 10 and disc portions 176, 178 so that hold down assembly 120 moves away from the analysis rotor on table 20 as indicated in FIG. 3. Transport mechanism 28 then moves the rotor 10 from analysis station 22 to auxiliary station 24 and moves a newly loaded rotor 10 from loading station 14 to analysis station 18 for the next analysis sequence.

While a particular embodiment of the invention has been shown and described, various modifications will be apparent to those skilled in the art, and therefore it is not intended that the invention be limited to the disclosed embodiment, or to details thereof, and departures may be made therefrom within the spirit and scope of the invention.

What is claimed is:

1. A centrifugal analyzer system that employs a centrifugal analyzer rotor in the concurrent analyses of a plurality of fluid samples, each centrifugal analyzer rotor having a body portion that has a top surface and that defines a circumferential array of elongated cuvettes, and each cuvette having a loading port, comprising an analysis compartment, loading and analysis stations spaced from one another in said analysis compartment, means at each of said loading and analysis stations for receiving a centrifugal analyzer rotor, drive means at said analysis station for spinning a rotor at at least one thousand rpm for mixing sample and reagent materials in cuvettes of a rotor and for maintianing rotation of a rotor at a slower rotational speed during an analysis interval for the concurrent analyses of a plurality of fluid samples, said drive means having a rotation axis, hold-down structure at said analysis station, said hold-down structure including a support aligned with the rotation axis of said drive means, an annular hold-down member secured to said support for free rotation relative to said support about said rotation axis of said drive means, for accommodation means coupled between said support and said hold-down member for seating said hold-down member in engagement with a top surface of a rotor on said rotor receiving means at said analysis station, said accommodation means including a self-aligning bearing assembly, guide structure for said support to maintain said support in alignment with the axis of said drive, and means operative to move said hold-down member along the rotation axis of said drive means between a seating position in engagement with a rotor and a second position spaced from a rotor on said rotor receiving means at said analysis station to permit a rotor to be removed from said drive means.

2. The analyzer system of claim 1 and further including a centrifugal analyzer rotor that has a smooth hard upper body surface in which two circumferential arrays of cuvette loading ports are defined, and said hold-down structure includes a port closing disc of material that has a durometer of at least about 30 (Shore A) and a surface roughness of at least about twenty microinches.

3. The analyzer system of claim 1 wherein said hold-down structure includes a port closing member of moderately resilient material and resilient means for imposing a biasing force on said port closing member.

4. The analyzer system of claim 3 further including a centrifugal analyzer rotor having a top surface in which a circumferential array of loading ports are disposed, and wherein the hardness of the rotor surface is greater than 50 Rockwell$_M$ and the durometer of said port closing member is at least about 30 (Shore A).

5. The analyzer system of claim 3 wherein said hold-down member moving means includes cam means for moving said hold-down member between said seating and second positions along the rotation axis of said drive means.

6. The analyzer system of claim 1 and further including a supply station containing a series of multi-cuvette rotor units, and transport mechanism movable between said supply, loading and analysis stations for transporting rotor units in correlated orientation between said stations.

7. The system of claim 6 wherein each said rotor defines a circumferential array of elongated radially extending cuvettes, each said elongated cuvette including structure defining a first chamber region for receiving a first constituent and a loading port through which said first constituent is introduced into said first chamber region, structure defining a second chamber region for receiving a second constituent, a second loading port through which said second constituent is introduced into said second chamber region, divider structure between said first and said chamber regions that defines a transfer passage between said first and second chamber regions through which said first constituent may be flowed into said second chamber region for forming a reaction product with said second constituent, and structure defining an analysis region adjacent the radially outer wall of said cuvette where said reaction product is subjected to analysis.

8. The system of claim 7 wherein said hold-down structure support includes a shaft aligned with the rotation axis of said drive means.

9. The analyzer system of claim 8 wherein said hold-down structure includes a port closing member of moderately resilient material and means for imposing a biasing force of about fifty grams on said port closing member.

10. The analyzer system of claim 9 wherein the hardness of the rotor surface in which said loading ports are disposed is greater than 50 Rockwell$_M$ and the durometer of said port closing member is about 40 (Shore A).

11. The system of claim 10 wherein said port closing member moving means includes cam means for moving said port closing member between said seating and second positions along the rotation axis of said drive means.

12. The system of claim 11 wherein said guide structure maintains the axis of said support shaft in alignment with the axis of said rotor drive table.

13. The system of claim 12 and further including means for positioning said hold-down member generally parallel to the surface of said rotor drive table when said hold-down member is in said second position.

14. The system of claim 7 wherein said analysis station includes a table for receiving a cuvette rotor, sensor means for providing output signals indicative of the angular position of said rotor at said analysis station, second drive means for indexing said table, and clutch means for disconnecting said second drive means from said table.

* * * * *